United States Patent [19]

Yamabe et al.

[11] 4,127,731
[45] Nov. 28, 1978

[54] PROCESS FOR PRODUCING FLUORINATED ACYL FLUORIDE HAVING AN ESTER GROUP

[75] Inventors: Masaaki Yamabe, Machida; Seiji Munekata; Yoshio Sugaya, both of Yokohama; Yukio Jitsugiri, Yokosuka, all of Japan

[73] Assignee: Asahi Glass Company Ltd., Tokyo, Japan

[21] Appl. No.: 739,727

[22] Filed: Nov. 8, 1976

[30] Foreign Application Priority Data

Nov. 11, 1975 [JP] Japan ................................. 50-134718

[51] Int. Cl.$^2$ ............................................. C07C 69/63
[52] U.S. Cl. .................................................... 560/192
[58] Field of Search ...................... 260/485 F; 560/192

[56] References Cited

U.S. PATENT DOCUMENTS

| | | | |
|---|---|---|---|
| 3,351,653 | 11/1967 | Carr et al. ....................... | 260/485 F |
| 3,461,155 | 4/1969 | Rice .................................... | 260/485 F |

OTHER PUBLICATIONS

Hauptschein et al., JACS 74, pp. 1974–1976 (1952).

Primary Examiner—Jane S. Myers
Attorney, Agent, or Firm—Oblon, Fisher, Spivak, McClelland & Maier

[57] ABSTRACT

A fluorinated acyl fluoride having an ester group which has the formula $$FOC(CF_2)_{n-1}CO_2R$$

wherein $n$ is 2 to 4 and R represents an alcohol residual group is produced by reacting a perfluorolactone having the formula

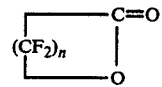

wherein $n$ represents an integer of 2 to 4, with an alcohol having the formula

ROH wherein R represents an alcohol residual group.

5 Claims, No Drawings

PROCESS FOR PRODUCING FLUORINATED ACYL FLUORIDE HAVING AN ESTER GROUP

BACKGROUND OF THE INVENTION

The present invention relates to a process for producing fluorinated acyl fluoride having an ester group. More particularly, it relates to novel fluorinated acyl fluoride having an ester group which is produced by reacting a specific perfluorolactone with an alcohol.

SUMMARY OF THE INVENTION

It is an object of the present invention to provide novel fluorinated acyl fluorides having an ester group which are useful in the field of the fluorinated compounds.

Another object of the invention is to provide a process for producing novel fluorinated acyl fluoride having an ester group in high yield.

DETAILED DESCRIPTION OF THE PREFERRED EMBODIMENTS

The novel fluorinated acyl fluorides having ester group (hereinafter referring to as fluorinated acyl fluoride ester) have the formula

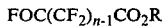

$FOC(CF_2)_{n-1}CO_2R$ wherein $n$ represents an integer of 2 to 4 and R represents an alcohol residual group.

The novel fluorinated acyl fluoride esters can be produced by reacting the following specific perfluorolactone with an alcohol in the following novel reaction.

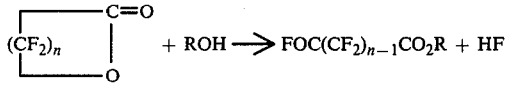

wherein $n$ and R are defined above.

The novel fluorinated acyl fluoride esters obtained by the process of the invention are useful as intermediates for various fluorinated compounds.

For example, perfluorovinyl ethers having an ester group can be produced by reacting the fluorinated acyl fluoride ester with hexafluoropropylene oxide and then thermally decomposing the reaction product.

The perfluorolactones used in the process of the invention can be produced by the reaction disclosed in U.S. Ser. No. 711978; British Ser. No. 32683/76; West German Ser. No. P 2635312.8; French Ser. No. 7623869; and Italian Ser. No. 26082A/76 and British Ser. No. 38457/76; West German Ser. No. P 2642824.0; and French Ser. No. 7628617.

That is, the perfluorolactone can be produced by reacting α,ω-diiodoperfluoroalkane or a perfluoroacyl halide having a terminal iodo group with a fuming sulfuric acid.

It is also possible to produce the perfluorolactone by heating a silver salt of perfluoroglutarate in the presence of iodine by the method of R. E. Banks et al. (JCS (C), 1967, 2333).

The alcohols as the other starting material can be various alcohols.

Suitable alcohols include alcohols having 1 to 8 carbon atoms. In the formula ROH, R can be an alkyl group having 1 to 8 carbon atoms and a straight chain or a branched chain aralkyl group and an aryl group, which can have an inert substituent.

The reaction of the perfluorolactone with the alcohol in the process of the invention can be carried out by diluting the starting material with an inert organic solvent.

The reaction of the perfluorolactone with the alcohol is remarkably vigorous. Accordingly, in order to selectively produce the object novel fluorinated acyl fluoride esters, it is preferable to carry out the reaction by diluting the starting material with an inert organic solvent.

The inert organic solvents should be inert to the alcohol, the perfluorolactone and the reaction product, and liquid under the reaction condition and miscible to the perfluorolactone and the alcohol, and can be any type solvent.

Suitable inert organic solvents include hydrocarbon nitriles having 2 to 12 carbon atoms such as propionitrile, benzonitrile, acetonitrile; aliphatic polyethers and alicyclic ethers having 4 to 16 carbon atoms such as ethyleneglycol dimethyl ether, diethyleneglycol dimethyl ether, dioxane and other polar solvents. It is also possible to use chlorofluoroalkane such as trichloromonofluoromethane and trichlorotrifluoroethane and other haloalkanes.

The dilution with the inert organic solvent can be carried out in desired manners. It is preferable to react the perfluorolactone with the alcohol after diluting both of the perfluorolactone and the alcohol.

The perfluorolactone is usually diluted in a range of about 0.1 to 10 ml/g preferably 0.5 to 3.0 ml/g of solvent/perfluorolactone.

The alcohol is usually diluted in a range of about 0.1 to 10 ml/ml preferably 1.0 to 5.0 ml/g of solvent/alcohol.

Of course, it is possible to dilute either the perfluorolactone or the alcohol before the reaction. It is also possible to react them by adding dropwise the perfluorolactone and the alcohol respectively into the inert organic solvent with uniformly stirring to cause the desired diluting condition.

The molar ratio of the alcohol to the perfluorolactone in the reaction can be selected as desired and is preferably in a range of less than 2 especially 0.3 to 1.7, more especially 0.5 to 1.5 in order to selectively produce the object novel fluorinated acyl fluoride ester.

It was reported that diethyl perfluorosuccinate was produced by reacting perfluorobutyrolactone with large excess ethanol (JACS, 74, P. 1974, 1952).

There is no disclosure nor suggestion on the novel fluorinated acyl fluoride esters as the adduct of the perfluorolactone and the alcohol of the invention.

In the process of the invention, the adducts of the perfluorolactone and the alcohol having the formula $FOC(CF_2)_{n-1}CO_2R$ can be selectively produced under selected conditions of (1) a molar ratio of the alcohol to the perfluorolactone; (2) a dilution with the inert organic solvent; (3) a kind of the solvent; (4) a reaction temperature etc.

The reaction of the alcohol with the perfluorolactone is preferably carried out under substantially anhydrous condition.

When water is present in the reaction system, the reaction of the perfluorolactone with water, is caused to produce $HOOC(CF_2)_{n-2}COOH$ or the reaction of the fluorinated acyl fluoride ester with water, whereby the yield of the fluorinated acyl fluoride ester is decreased.

Moreover, the corrosion of the reactor is disadvantageously caused.

The reaction temperature can be selected. Since the exothermic reaction of the perfluorolactone with the alcohol causes heat, it is preferable to react them at −80° C. to +100° C. preferably −40° C. to +50° C. especially −60° C. to +70° C. in order to react them under controlled conditions.

Thus, the production of the undesired diesters can be inhibited to obtain the novel fluorinated acyl fluoride ester in high yield.

In the process of the invention, hydrogen fluoride is produced as shown in the reaction scheme of the reaction of the perfluorolactone with the alcohol. The hydrogen fluoride can be easily removed by the use of a hydrogen fluoride uptaking agent such as NaF or the distillation after the reaction.

In usual, it is preferable to previously add the hydrogen fluoride uptaking agent in the reaction system so as to smoothly treat the reaction mixture after the reaction.

The hydrogen fluoride uptaking agents are preferably fluorides of an element in the Group I-A of the periodic table such as NaF.

The reactors are preferably made of nickel steels such as stainless steel and Hastelloy especially a lining thereof. It is difficult to use a reactor made of glass because of the by-product of hydrogen fluoride. It is necessary to use the material which is not corroded with hydrogen fluoride.

It is preferable to carry out the reaction under substantially anhydrous condition. Accordingly, the starting materials, the inert organic solvent, the hydrogen fluoride uptaking agent and the reactor are preferably treated by suitable dehydrating method and drying method before using them.

The process of the invention can be carried out by desired operations under desired conditions. It is possible to react the perfluorolactone with the alcohol by charging them at the predetermined amounts in the reactor. It is preferable to gradually or sequentially add the alcohol diluted with a desired amount of the solvent into the perfluorolactone diluted with a desired amount of the solvent.

In order to selectively produce the novel fluorinated acyl fluoride ester under the smooth reaction, it is preferable to employ a desired uniformly mixing method with vigorously stirring the reaction system.

After the reaction, the reaction mixture was filtered to remove the solid components from the reaction mixture and the filtrate is distilled to separate the object product.

The invention will be further illustrated by certain specific examples which are included for purposes of illustration only and not intended to be limiting unless otherwise specified.

EXAMPLE 1

In an autoclave made of stainless steel, 208 g (4.95 mole) of sodium fluoride (NaF: pure) was charged and dried. In the autoclave, 400 ml of anhydrous diethyleneglycol dimethyl ether was charged and the mixture was cooled to −40° C., and then, 400 g (2.26 mole) of perfluoro-γ-butyrolactone was added in a liquid form.

The temperature in the autoclave was maintained at −40° C. and a mixture of ethanol and diethyleneglycol dimethyl ether, (2.5/1.0 by volume of the solvent/ethanol) was continuously fed with vigorously stirring until providing 1.2 molar ratio of ethanol to perfluoro-γ-butyrolactone. The reaction was ceased at this ratio.

The reaction mixture in the autoclave was filtered to separate the solid and the filtrate was distilled to obtain 3-carboethoxy perfluoropropionyl fluoride having a boiling point of 110° to 112° C. (760 mmHg) in the yield of 64 mole % (based on perfluoro-γ-butyrolactone).

EXAMPLE 2

In accordance with the process of Example 1, sodium fluoride, diethyleneglycol dimethyl ether and perfluoro-γ-butyrolactone were charged in the autoclave. A mixture of ethanol and diethyleneglycol dimethyl ether (2.5/1.0 by volume of the solvent/ethanol) was continuously fed with vigorously stirring until providing 1.0 molar ratio of ethanol to perfluoro-γ-butyrolactone. The reaction was ceased at this ratio.

In accordance with the process of Example 1, the isolation was carried out to obtain 3-carboethoxy perfluoropropionyl fluoride in the yield of 60 mole % (based on perfluoro-γ-butyrolactone).

EXAMPLE 3

In an autoclave made of stainless steel, 208 g (4.95 mole) of sodium fluoride (NaF:pure) was charged and dried. In the autoclave, 400 ml of trichlorotrifluoroethane (R-113) was charged and the mixture was cooled to −20° C., and then, 400 g (2.06 mole) of perfluoro-γ-butyrolactone was added in a liquid form.

The temperature in the autoclave was maintained at −20° C. and a mixture of ethanol and trichlorotrifluoroethane (2.5/1.0 by volume of the solvent/ethanol) was continuously fed with vigorously stirring until providing 1.2 molar ratio of ethanol/perfluoro-γ-butyrolactone. The reaction was ceased at this ratio.

In accordance with the process of Example 1, the isolation was carried out to obtain 3-carboethoxy perfluoropropionyl fluoride in the yield of 50 mole % (based on perfluoro-γ-butyrolactone).

EXAMPLE 4

In accordance with the process of Example 3, sodium fluoride, trichlorotrifluoroethane and perfluoro-γ-butyrolactone were charged in the autoclave, and a mixture of methanol and trichlorotrifluoroethane (5/1 by volume of the solvent/methanol) was continuously fed with stirring at −20° C. until providing 1.1 molar ratio of methanol to perfluoro-γ-butyrolactone. The reaction was ceased at this ratio.

In accordance with the process of Example 1, the isolation was carried out to obtain 3-carbomethoxy perfluoropropionyl fluoride in the yield of 40 mole %(based on perfluoro-γ-butyrolactone).

EXAMPLE 5

In accordance with the process of Example 1, sodium fluoride, diethyleneglycol dimethyl ether and perfluoro-γ-butyrolactone were charged in the autoclave, and the mixture of ethanol and diethyleneglycol dimethyl ether (2.5/1 by volume of the solvent/ethanol) was continuously fed with stirring at 6° to 10° C. until providing 1.1 molar ratio of ethanol perfluoro-γ-butyrolactone. The reaction was ceased at this ratio.

In accordance with the process of Example 1, the isolation was carried out to obtain 3-carboethoxy perfluoropropionyl fluoride in the yield of 64 mole % (based on perfluoro-γ-butyrolactone).

EXAMPLE 6

In a 100 liter autoclave made of stainless steel, 9.6 kg of dried sodium fluoride, 26 liter of anhydrous diethyleneglycol dimethyl ether were charged and the mixture was cooled to $-40°$ C., and then 26.2 kg of perfluoro-$\gamma$-butyrolactone was charged.

The temperature in the autoclave was maintained at $-5°$ C. and a mixture of methanol and diethyleneglycol dimethyl ether (2.5/1.0 by volume of the solvent/ethanol) was continuously fed with vigorously stirring until providing 1.16 molar ratio of ethanol to perfluoro-$\gamma$-butyrolactone. The reaction was ceased at this ratio.

The reaction mixture was filtered and the components in the reaction mixture were measured by the gas-chromatography analysis. As the result, the conversion of perfluoro-$\gamma$-butyrolactone was 89.3% and the selectivity of 3-carboethoxy perfluoropropionyl fluoride was 88.9%. The reaction product was distilled to obtain 21.2 kg of 3-carboethoxy perfluoropropionyl fluoride in the yield of 71.3 mole %(based on perfluoro-$\gamma$-butyrolactone).

EXAMPLE 7

In a 5 liter autoclave made of stainless steel, 700 g of dried sodium fluoride and 1150 g of anhydrous diethyleneglycol dimethyl ether were charged and the mixture was cooled to $-40°$ C., and then 1380 g of perfluoro-$\gamma$-butyrolactone was charged.

The temperature in the autoclave was maintained at $-10°$ C. and a 12.5 wt. % solution of methanol in diethyleneglycol dimethyl ether was continuously fed with vigorously stirring until providing 0.9 molar ratio of methanol to perfluoro-$\gamma$-butyrolactone. The reaction was ceased at this ratio.

The reaction mixture was distilled to obtain 3-carbomethoxy perfluoropropionyl fluoride having a boiling point of 96° to 97° C. in the yield of 61 mole %(based on perfluoro-$\gamma$-butyrolactone).

What is claimed is:

1. A process for producing a fluorinated acyl fluoride having an ester group which has the formula $$FOC(CF_2)_{n-1}CO_2R$$

wherein $n$ represents an integer of from 2 to 4 and R represents an alcohol residual group which comprises reacting under substantially anhydrous conditions a perfluorolactone having the formula

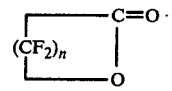

wherein $n$ represents an integer of from 2 to 4 with an alcohol having the formula ROH wherein R represents an alkyl, aralkyl or aryl group having up to 8 carbon atoms, wherein the molar ratio of alcohol to perfluorolactone is less than 2, and wherein the perfluorolactone and/or the alcohol are respectively diluted with anhydrous inert organic solvent before the reaction.

2. A process according to claim 1, wherein the perfluorolactone and the alcohol are respectively added in the anhydrous inert organic solvent.

3. A process according to claim 1, wherein a hydrogen fluoride uptaking agent is added in the reaction system.

4. A process according to claim 3, wherein sodium fluoride is added as the hydrogen fluoride uptaking agent.

5. A process according to claim 1 wherein the anhydrous inert organic solvent is diethyleneglycol dimethylether.

* * * * *